(12) United States Patent
Park

(10) Patent No.: US 12,036,127 B2
(45) Date of Patent: Jul. 16, 2024

(54) PROSTHETIC FEMORAL HEAD AND METHOD OF MAKING THE SAME

(71) Applicant: Lento Medical Inc., Houston, TX (US)

(72) Inventor: Ilwhan Park, Katy, TX (US)

(73) Assignee: Lento Medical Inc., Houston, TX (US)

( * ) Notice: Subject to any disclaimer, the term of this patent is extended or adjusted under 35 U.S.C. 154(b) by 183 days.

(21) Appl. No.: 17/724,925

(22) Filed: Apr. 20, 2022

(65) Prior Publication Data

US 2023/0338154 A1     Oct. 26, 2023

(51) Int. Cl.
*A61F 2/36* (2006.01)
*A61F 2/30* (2006.01)
*B29C 45/14* (2006.01)

(52) U.S. Cl.
CPC .............. *A61F 2/3609* (2013.01); *A61F 2/36* (2013.01); *A61F 2002/30327* (2013.01); *A61F 2002/30769* (2013.01); *A61F 2002/30784* (2013.01); *A61F 2002/30957* (2013.01); *A61F 2002/30971* (2013.01); *A61F 2002/3613* (2013.01); *A61F 2002/3652* (2013.01); *A61F 2310/00017* (2013.01); *A61F 2310/00023* (2013.01); *A61F 2310/00029* (2013.01); *A61F 2310/00059* (2013.01); *A61F 2310/00179* (2013.01); *B29C 2045/14967* (2013.01); *B29K 2715/003* (2013.01)

(58) Field of Classification Search
CPC ....... A61F 2002/3605; B29C 45/14631; B29C 2045/14967
See application file for complete search history.

(56) References Cited

U.S. PATENT DOCUMENTS

| | | | |
|---|---|---|---|
| 5,549,700 A * | 8/1996 | Graham | B29C 70/84 403/135 |
| 6,793,681 B1 | 9/2004 | Pope et al. | |
| 9,095,438 B1 | 8/2015 | Wait | |
| 9,271,839 B2 | 3/2016 | Armacost et al. | |
| 9,333,083 B2 | 5/2016 | Li et al. | |
| 9,427,268 B2 | 8/2016 | Ye | |
| 9,763,791 B2 | 9/2017 | Lawrynowicz et al. | |
| 9,974,657 B2 | 5/2018 | McMinn | |
| 2004/0199250 A1* | 10/2004 | Fell | A61F 2/38 623/908 |
| 2013/0006354 A1* | 1/2013 | Pressacco | A61F 2/30 623/11.11 |

(Continued)

*Primary Examiner* — Ariana Zimbouski
*Assistant Examiner* — Yasniary De La Caridad Morales
(74) *Attorney, Agent, or Firm* — Mark Protsik; Thomas Schneck

(57) ABSTRACT

A femoral head prosthesis is a multilayer composite having a metal neck stem component thread or press fit into a hollow rigid shell of metal or ceramic, a polymeric core filling the interior volume under the hollow rigid shell and around a forward part of the neck stem, and a smooth, void-free polymeric articulation layer of at most 12 mm over the exterior of the shell. The prosthesis is formed by a polymeric molding process wherein polymerizing resin or heated thermoplastic material is flowed in a mold through a set of holes through the hollow shell into the interior volume and around the shell's exterior. Once the resin has cured or the thermoplastic cooled, the stem, core, shell and articulation layer collectively form an integral prosthesis of a desired head diameter matching a patient's anatomy.

11 Claims, 3 Drawing Sheets

(56) References Cited

U.S. PATENT DOCUMENTS

2020/0129298 A1\* 4/2020 Kavolus, II ............. C08L 23/06
2021/0045881 A1   2/2021 Melozzi
2022/0313443 A1\* 10/2022 Keefer ................ A61F 2/30942

\* cited by examiner

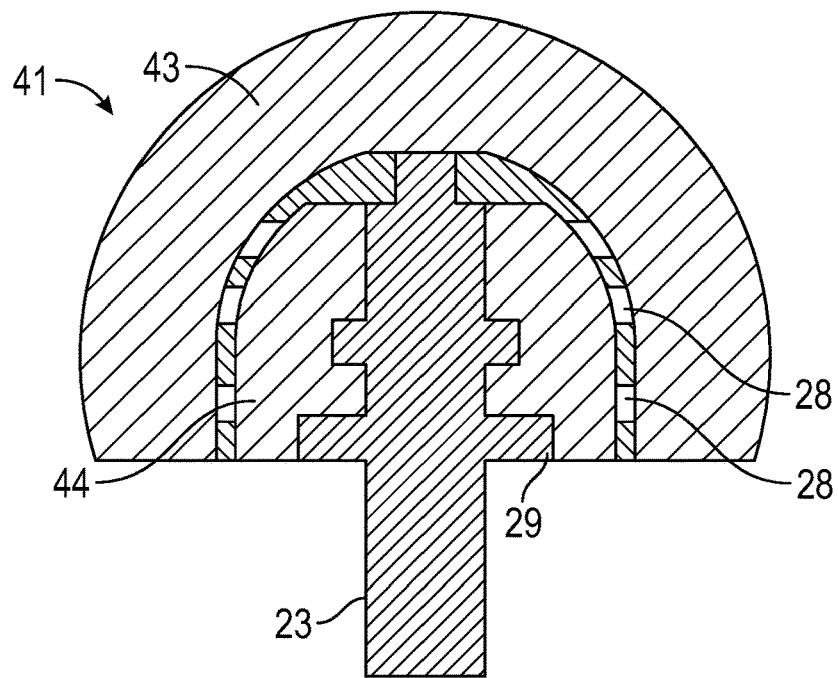
FIG. 5
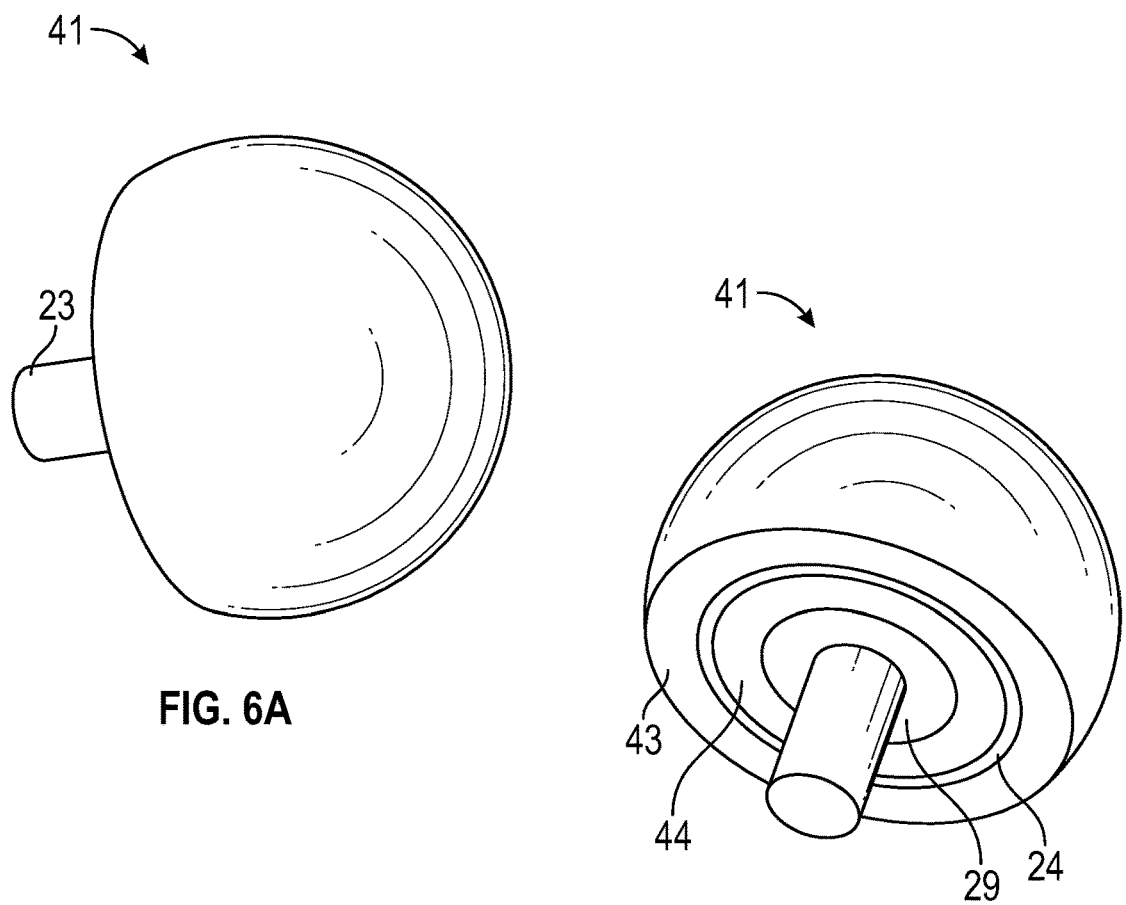
FIG. 6A
FIG. 6B

PROSTHETIC FEMORAL HEAD AND METHOD OF MAKING THE SAME

TECHNICAL FIELD

The present invention relates to medical prostheses (i.e., artificial substitutes or replacements for parts of the body) that are surgically implantable into the body, and more specifically to femoral head prostheses for hip joints and the methods of making such prosthetic femoral heads.

BACKGROUND ART

One very common femoral prosthesis for total hip replacement of the prior art is seen in FIG. 1. The prosthesis 11 has an integral femoral stem portion 12 and femoral neck portion 13, which are either integral with or connected to a femoral head portion 14. The femoral head portion 14 is often in the form of a unitary solid metal ball with a smooth wear-resistant surface that interacts with hip acetabulum (or acetabular prosthesis) to form a complete hip joint. A solid metal femoral head adds weight to the prosthesis. Efforts to reduce the weight have included forming femoral heads with ceramic or polymeric elements replacing some of the metal. However, in some cases such femoral heads suffer from a reduced average lifetime, either from increased surface wear or potential damage due to ceramic brittleness.

In U.S. Pat. No. 9,333,083, Li et al. describe a hip joint with an acetabulum and femoral ball head, where the latter is a multi-layer composite structure of alumina-based sintered ceramic materials. The head structure has a ceramic spherical shell layer, a ceramic transitional layer, and a toughened ceramic inner core obtained through a powder co-injection molding process using a polymer binder followed by sintering of the molded ceramic material.

In U.S. Pat. No. 9,763,791, Lawrynowicz et al. describe a prosthesis head with a composite structure of a hollow metal shell filled with an interior polymeric material. Except for a conically tapered socket recess, the inner shell is otherwise completely filled with the polymer, which may have a porous structure.

SUMMARY DISCLOSURE

A femoral head prosthesis is provided having a base in the form of a rigid hollow shell with a set of holes through the surface thereof, a polymeric core within an interior of the hollow shell, and a polymeric articulation layer that coats an exterior of the hollow shell, the articulation layer having a thickness of at most 12 millimeters and lacking any voids or defects therein to form a smooth durable surface. The base is coupled to a prosthesis neck shaft. The rigid hollow shell forming the base is typically composed of a biocompatible metal (although biocompatible ceramic materials might also be used) and may have a shell thickness in a range from 1.5 to 2.5 millimeters, with the set of holes through the shell having a diameter in a range from 3 to 5 millimeters. The composition of the polymeric core and polymeric articulation layer is typically selected from any of polyether ether ketone (PEEK), polyethylene, and ultra-high-molecular-weight polyethylene (UHMWPE). The polymeric core, hollow shell base, and polymeric articulation layer collectively will typically have an overall diameter in a range from 32 to 40 millimeters.

A method of making a femoral head prosthesis comprises the steps of (1) providing a base in the form of a rigid hollow shell with a set of holes through the surface thereof; (2) molding a polymerizing resin or pre-formed heated thermoplastic onto the base, the resin or hot thermoplastic flowing through the holes in the shell to fill an interior of the hollow shell, the resin or hot thermoplastic also flowing over an exterior surface of the hollow shell to form a layer on the shell with a thickness of at most 12 millimeters; and (3) allowing the resin to cure or the thermoplastic to cool into a polymeric core within the interior of the now-filled hollow shell and a polymeric articulation layer over the exterior of the hollow shell, the articulation layer lacking any voids or defects therein to form a smooth durable surface. Prior to the molding step, the base will typically first be coupled to a prosthesis neck shaft, wherein the polymerizing resin or heated thermoplastic subsequently flows through the holes into the interior of the hollow shell surrounds that neck shaft, securing it in place to the resulting prosthesis femoral head.

BRIEF DESCRIPTION OF THE DRAWINGS

FIG. 5 is a side sectional view and FIGS. 6A and 6B are respective front and underside perspective views of the completed femoral head after the resin in FIG. 4 has cured and polymerized.

DETAILED DESCRIPTION

Figure 1:
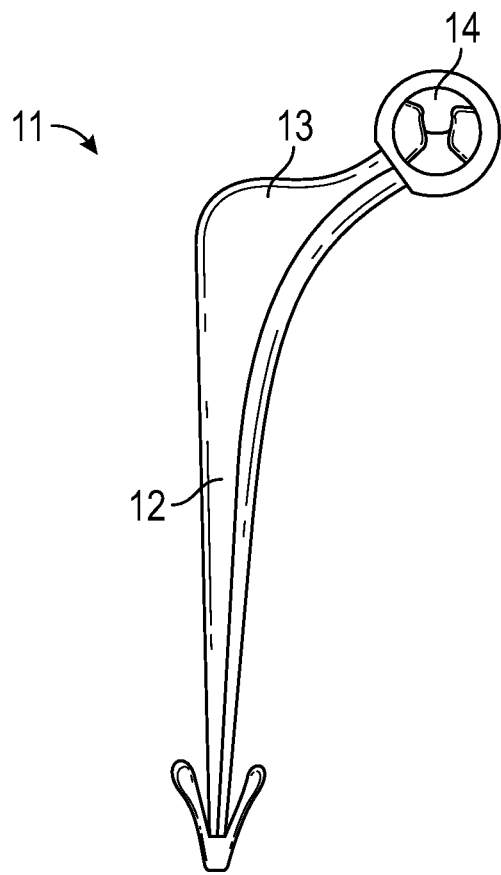
FIG. 1 is a side view of a total hip prosthesis of the prior art with a femoral ball head attached to an integral stem and neck component.
Figure 2:
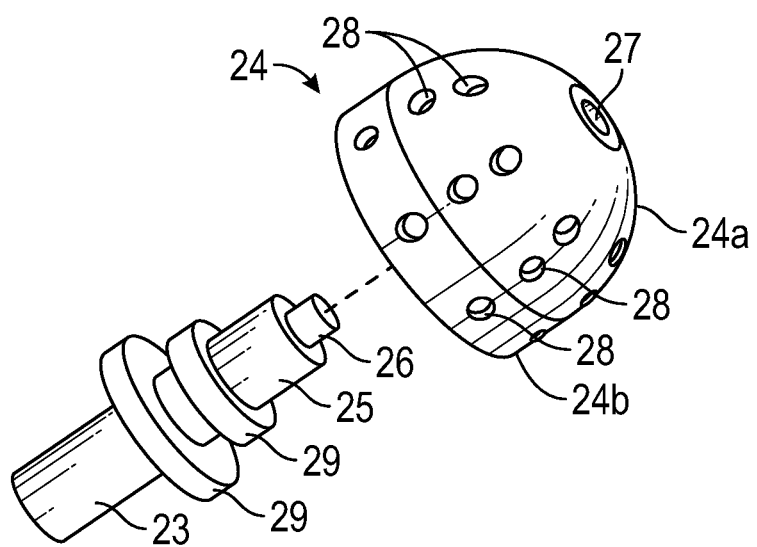
FIG. 2 is a perspective view of a femoral head shell detached from a corresponding femoral neck shaft component for creation of a prosthesis in accord with the present invention.
Figure 3A:
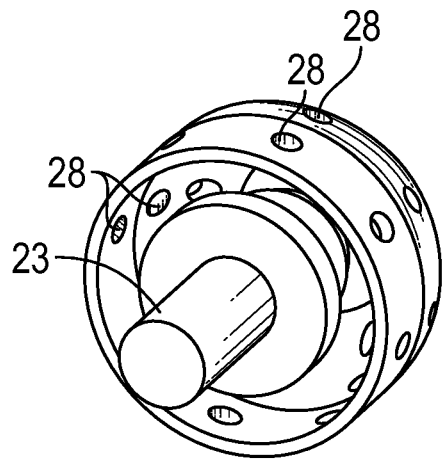
FIGS. 3A and 3B are two different perspective views of the femoral head shell and attached femoral neck shaft of FIG. 2, respectively showing an interior shell volume and front exterior attachment.
Figure 3B:
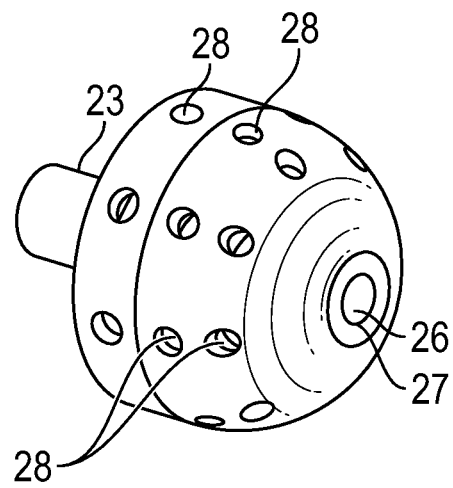

With reference to FIGS. 2, 3A and 3B, a prosthetic femoral head base 24 in the form of a rigid shell is seen to attach to a prosthetic femoral neck shaft component 23. The rigid shell 24 has a general convex hemispheric shape 24a, possibly terminating in a short cylindrical section 24b. The shell 24 has a thickness in a range from 1.5 to 2.5 millimeters. A set of holes 28 through the shell 24 have a diameter in a range from 3 to 5 millimeters, sufficiently large to allow passage of polymerizing resin into the interior volume within an underside of the shell 24.

The prosthetic femoral neck shaft component 23 has an end 26 that can be threaded or press fit into a front opening 27 of the shell 24, so that the end 26 of the shaft 23 is generally flush with the exterior hemispheric surface 24a of the shell 24. Once the polymeric coating has been applied and cured, the neck shaft 23 and shell 24 will be permanently secured to one another as an integral head-and-neck prosthetic component. The neck shaft component 23 typically also has a series of spaced disks 29 projecting outward from and integral with a central shaft 25. These integral disks 29 will help to hold the polymerizing resin material received in the shell interior until it cures, and then lock the neck 24 and head shell 25 securely together once the polymeric material has cured.

Biocompatible metals and alloys for the rigid shell 24 and neck shaft 23 may include cobalt-chromium alloys (mainly Co-28Cr-6Mo, but others are possible), titanium (Ti) and titanium alloys (mainly Ti-6Al-4V and Ti-15Zr, but others are possible). Cobalt-chromium alloys and titanium materials tend to be relatively hard to fabricate. But, the shell material may also be formed from any of various medical-grade stainless steels, which are much easier to fabricate, make holes in, etc. Currently, the most widely used medical-grade stainless steel is stainless steel 316 (UNS S31603/SAE 316L/ASTM A240), which is a chromium-nickel-molybdenum austenitic stainless steel with ~65% Fe, 16-18% Cr, 10-14% Ni, 2-3% Mo, and specified small amounts of manganese, silicon, carbon, and other elements. More recently, several nitrogen-strengthened, low-nickel or nickel-free, austenitic stainless steels have become available for use in surgical implants and orthopedic prostheses. Among these are stainless steel 108 (UNS S29108/ASTM F2229-20) with ~54% Fe, 21-24% Mn, 19-23% Cr, 0.5-1.5% Mo, 0.85-1.10% N, and small amounts of silicon, carbon, and other elements (and notably not more than 0.10% Ni), as well as ASTM F2581-12 stainless steel (UNS S29225) with ~67% Fe, 16.5-18.0% Cr, 9.5-12.5% Mn, 2.7-3.7% Mo, 0.45-0.55% N, and small amounts of silicon, carbon, and other elements (and again notably not more than 0.05% Ni). The usual presence of molybdenum in all these medical-grade stainless steels serves to provide corrosion resistance in the normal saline environment of the human body. The list of suitable biocompatible metal alloys is not exhaustive. Many more biocompatible metals are expected to become available and be approved for medical devices, and the invention is not limited to any specific one of them.

The neck shaft 23 and shell 24 can be selected as different materials, i.e., the shell material can be medical-grade stainless steels that can be easily fabricated, and the neck material can be cobalt-chromium or titanium alloys. Although both materials are medical-grade biocompatible material, there is potential electrolyte chemical reaction between the two materials with joint or synovial fluid as an electrolyte solution. However, the plastic mold surrounding the two materials will prevent the joint fluid from formation of any potential electrolyte chemical reaction. Furthermore, even if an electrolyte chemical reaction between two materials were to happen, the plastic mold can block any ionized or corroded species from leaking into the human body.

The rigid shell 24, especially since it will be reinforced with the polymeric material both within its interior volume and as an exterior coating layer, might also be composed of a biocompatible ceramic material. These include both high-density alumina ($Al_2O_3$) and yttria-stabilized zirconia ($ZrO_2$ doped with $Y_2O_3$). Other similar ceramic materials are expected to become available and eventually be approved for medical devices, and the invention is not limited to any specific one of them. The key requirement is that the shell simply be able to serve as a base for receiving the polymeric core and surface coating.

Figure 4:
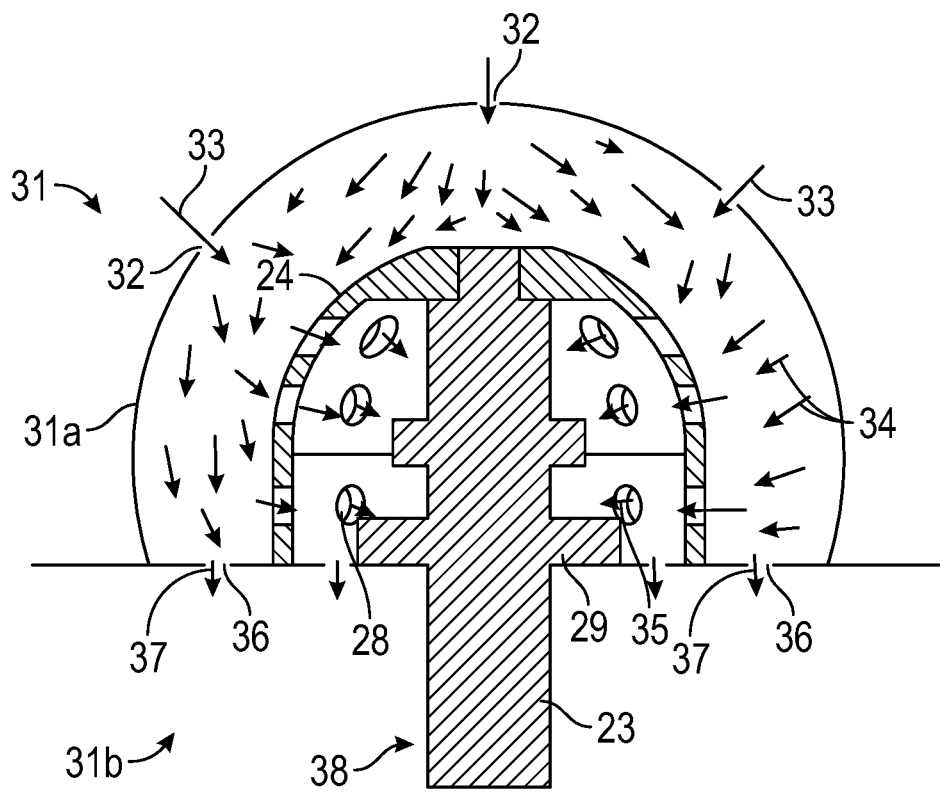
FIG. 4 is a side sectional view of the attached femoral head shell and femoral neck shaft of FIG. 2 in a mold receiving a flow of polymerizing resin, with some of that resin flowing through openings in the shell into the interior shell volume and the remainder of the resin forming an exterior polymer coating over the femoral head shell.

With reference to FIG. 4, the attached neck shaft 23 and shell 24 are placed in a mold 31. The neck shaft 23 may be seated in a slot 38 in a bottom part 31b of the mold 31 so that one of the neck disks 29 sits on a surface of the mold's bottom part 31b. Polymerizing resin will be introduced into the mold 31 primarily to create a polymeric articulation layer that coats an exterior of the hollow shell 24. That articulation layer is intended to have a thickness of at most 12 millimeters and lack any voids or defects therein to form a smooth durable surface. Accordingly, there is a space between the outer surface of the shell 24 and an inner surface of an upper portion 31a of the mold 31, which itself is at most 12 millimeters deep. That is, the distance between the shell and the upper mold 31a is not more than 12 millimeters.

The space between the shell and mold is filled with polymerizing resin or pre-formed heated thermoplastic 33 through openings 32 in the upper mold 31a. The resin or thermoplastic 33 flows within the articulation space as indicated by the arrows 34 and flows into the hollow interior volume of the shell 24 through the holes 28 in the shell 24, as indicated by arrows 35. The outward extending disks 29 on the neck shaft 23 retain most of the received resin 33 in the interior volume of the shell 24 and fill that volume even into the spaces between the disks 29. However, to ensure that all air is allowed to escape and the resin or thermoplastic lacks bubbles or other voids, holes 36 through the bottom portion 31b of the mold 31 do allow some of the resin or thermoplastic material 37 to escape along with the original air.

Once the mold 31 has been filled with the polymerizing resin, it is allowed to cure to form the polymer core and articulation layer of the prosthetic femoral head. Curing may include the use of heat in addition to time, according to the chosen polymer and precursor monomer resins and well-known techniques. Where the chosen biocompatible polymer is a thermoplastic material, the pre-formed polymer can be heated, applied hot directly into the mold, then allowed to cool.

Biocompatible polymers that may be chosen include any of polyether ether ketone (PEEK), polyethylene, and ultra-high-molecular-weight polyethylene (UHMWPE). It is well-known for example that PEEK may be formed, in one instance, using a mixture of 4,4'-difluorobenzophenone and disodium bisphenolate in a polar aprotic solvent such as diphenyl sulfone. Each of the biocompatible polymers mentioned above are also thermoplastics.

With reference to FIGS. 5, 6A and 6B, the resulting prosthetic component 41 after being removed from the mold has a largely hemispheric shape with a portion of the original neck stem 23 projecting out of the hemispheric flat bottom surface coincident with original disk 29. It has an overall diameter in a range typically from 32-40 mm, depending on the anatomical size of a patient's femoral head to be replaced. The prosthesis is therefore a multilayer composite of biocompatible metal and/or ceramic (the neck stem 23 and the shell 24) and of biocompatible polymer in both the interior volume 44 under the formerly hollow (now filled) shell and the exterior articulation layer 43 over the exterior of the shell 24. The polymer material 44 in the interior volume beneath the shell 24 is permitted to have voids or other molding defects. As it is protected from wear by the other composite layers, this zone of material has adequate structural stability. Because the core 44 is a polymer instead of metal or ceramic, the weight of the prosthetic component 41 is substantially reduced compared to existing all-metal or coated-metal-core-type hip prostheses. The exterior articulation layer 43 however, does need to be free of voids or other molding defects to give it high wear resistance and a smooth hemispheric articulating surface for the joint. Restricting the thickness of the exterior polymer layer 43 to a range of 8 to 12 mm can significantly aid in achieving a substantial absence of any such voids or defects.

What is claimed is:

1. A method of making a femoral head prosthesis, comprising:
providing a base in the form of a rigid hollow shell with a set of holes through its surface to an interior thereof;

molding a polymeric material onto the base, the polymeric material flowing through the holes in the shell to fill the interior of the hollow shell, the polymeric material also flowing over an exterior surface of the hollow shell to form a layer coating the exterior surface of the shell with a thickness of at most 12 millimeters; and allowing the polymeric material to solidify into a polymeric core within the interior of the now-filled hollow shell and a polymeric articulation layer over the exterior of the hollow shell, the articulation layer lacking any voids or defects therein to form a smooth durable surface.

2. The method as in claim 1, wherein the rigid hollow shell is composed of a biocompatible metal.

3. The method as in claim 2, wherein the biocompatible metal is selected from any of cobalt, chromium, titanium, alloys thereof, and medical-grade stainless steel.

4. The method as in claim 1, wherein the rigid hollow shell is composed of a biocompatible ceramic.

5. The method as in claim 1, wherein the rigid hollow shell has a shell thickness in a range from 1.5 to 2.5 millimeters.

6. The method as in claim 1, wherein the set of holes through the shell have a diameter in a range from 3 to 5 millimeters.

7. The method as in claim 1, wherein the polymeric material is selected from any of polyether ether ketone (PEEK), polyethylene, and ultra-high-molecular-weight polyethylene (UHMWPE).

8. The method as in claim 7, wherein the polymeric material is formed from a polymerizing resin, which after molding is allowed to cure.

9. The method as in claim 7, wherein the molding involves a flow of a heated thermoplastic, which is subsequently allowed to cool.

10. The method as in claim 1, wherein, prior to molding the polymeric material, the base is first coupled to a prosthesis neck shaft, the polymeric material flowing through the holes into the interior of the hollow shell surrounding the neck shaft.

11. The method as in claim 1, wherein the polymeric core, hollow shell base, and polymeric articulation layer collectively have an overall diameter in a range from 32 to 40 millimeters.

* * * * *